United States Patent [19]
Dwyer et al.

[11] Patent Number: 5,277,916
[45] Date of Patent: Jan. 11, 1994

[54] TETRACYCLINE DOSAGE FORM

[75] Inventors: Mark Dwyer; Mark C. Fisher; Angelo M. Morella, all of Adelaide, Australia

[73] Assignee: F. H. Faulding & Co., Ltd., North Adelaide, Australia

[21] Appl. No.: 523,239

[22] Filed: May 14, 1990

Related U.S. Application Data

[63] Continuation-in-part of Ser. No. 304,954, Feb. 1, 1989, abandoned.

[30] Foreign Application Priority Data

Feb. 1, 1988 [AU] Australia ............................. PI6511

[51] Int. Cl.$^5$ ........................... A61K 9/28; A61K 9/32
[52] U.S. Cl. ..................................... 424/494; 424/468; 424/470; 424/474; 424/479; 424/480; 424/482; 424/490; 424/493; 424/497
[58] Field of Search ............... 424/474, 494, 479, 493, 424/497, 468, 470, 480, 482, 490

[56] References Cited

U.S. PATENT DOCUMENTS

| | | | |
|---|---|---|---|
| 3,499,959 | 3/1970 | Corn | 424/496 |
| 3,538,214 | 11/1970 | Polli | 424/473 |
| 4,606,909 | 8/1986 | Bechgaard et al. | 424/482 |
| 4,837,030 | 6/1989 | Valorose, Jr. et al. | 424/456 |

FOREIGN PATENT DOCUMENTS

1568837 6/1980 United Kingdom .

OTHER PUBLICATIONS

A. A. El-Sayed, et al. (Aug. 1978) *Manu. Chem. Aero. News*, pp. 52-54, 1978.
Saurabh J. Desal, et al. (1966) *J. Pharm. Sciences*, vol. 55, No. 11, pp. 1224-1229.
Saurabh J. Desal, et al. *J. Pharm. Sciences*, vol. 55, No. 11, pp. 1230-1234.
T. Higuchi (1963) *J. Pharm. Sciences*, vol. 55, No. 11, pp. 1245-1249.
E. Nelson (1959) *J. Am. Pharma. Assoc.*, vol. XLVIII(2), pp. 96-103.

*Primary Examiner*—Thurman K. Page
*Assistant Examiner*—Amy Hulina
*Attorney, Agent, or Firm*—Darby & Darby

[57] ABSTRACT

A tetracycline pharmaceutical composition having a core element containing a tetracycline antibiotic and a core coating which dissolves more slowly in the stomach than in the intestine. Administration of the composition to a human results in drug concentrations in the blood which are bioequivalent to those achieved with immediate release formulations.

18 Claims, 11 Drawing Sheets

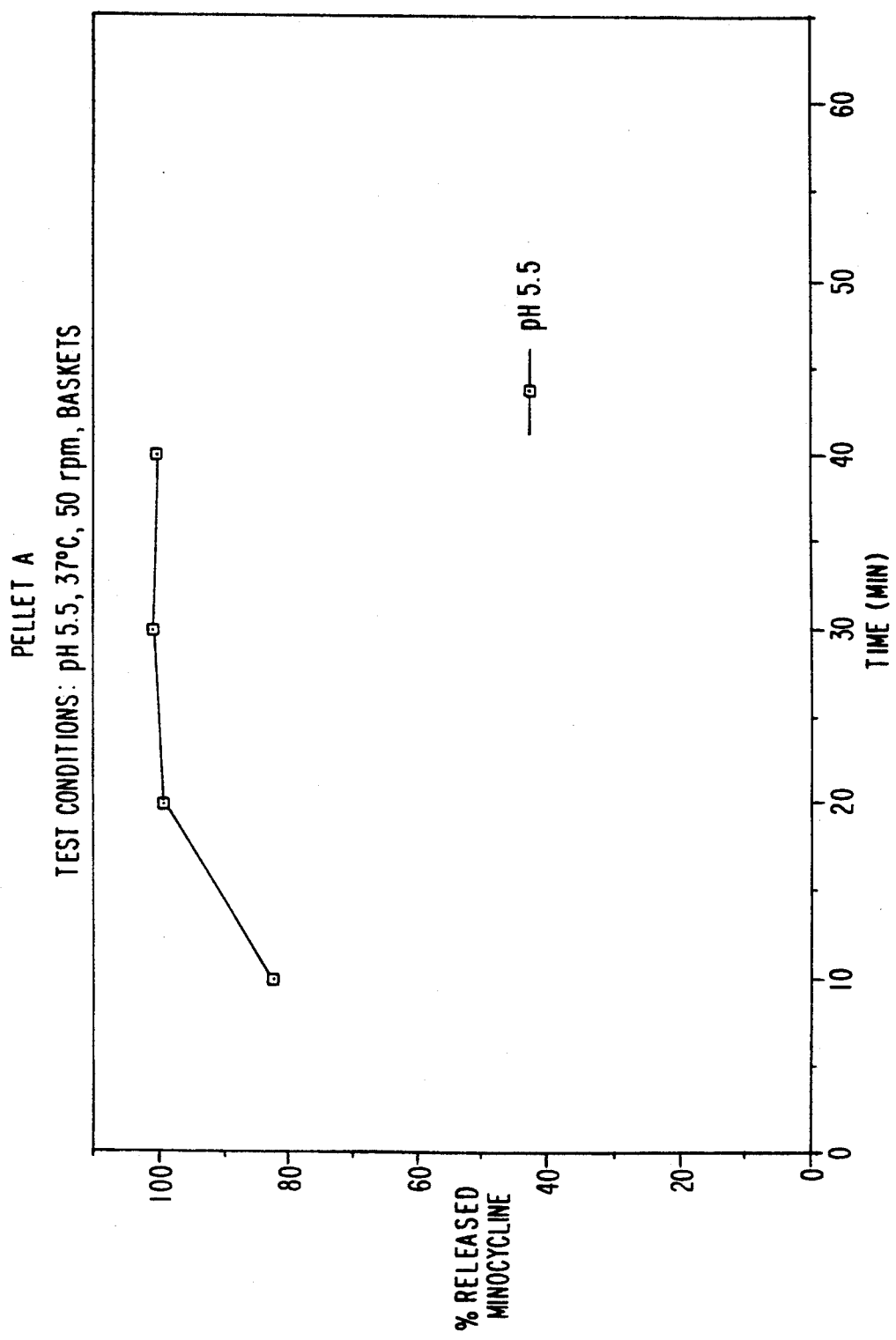

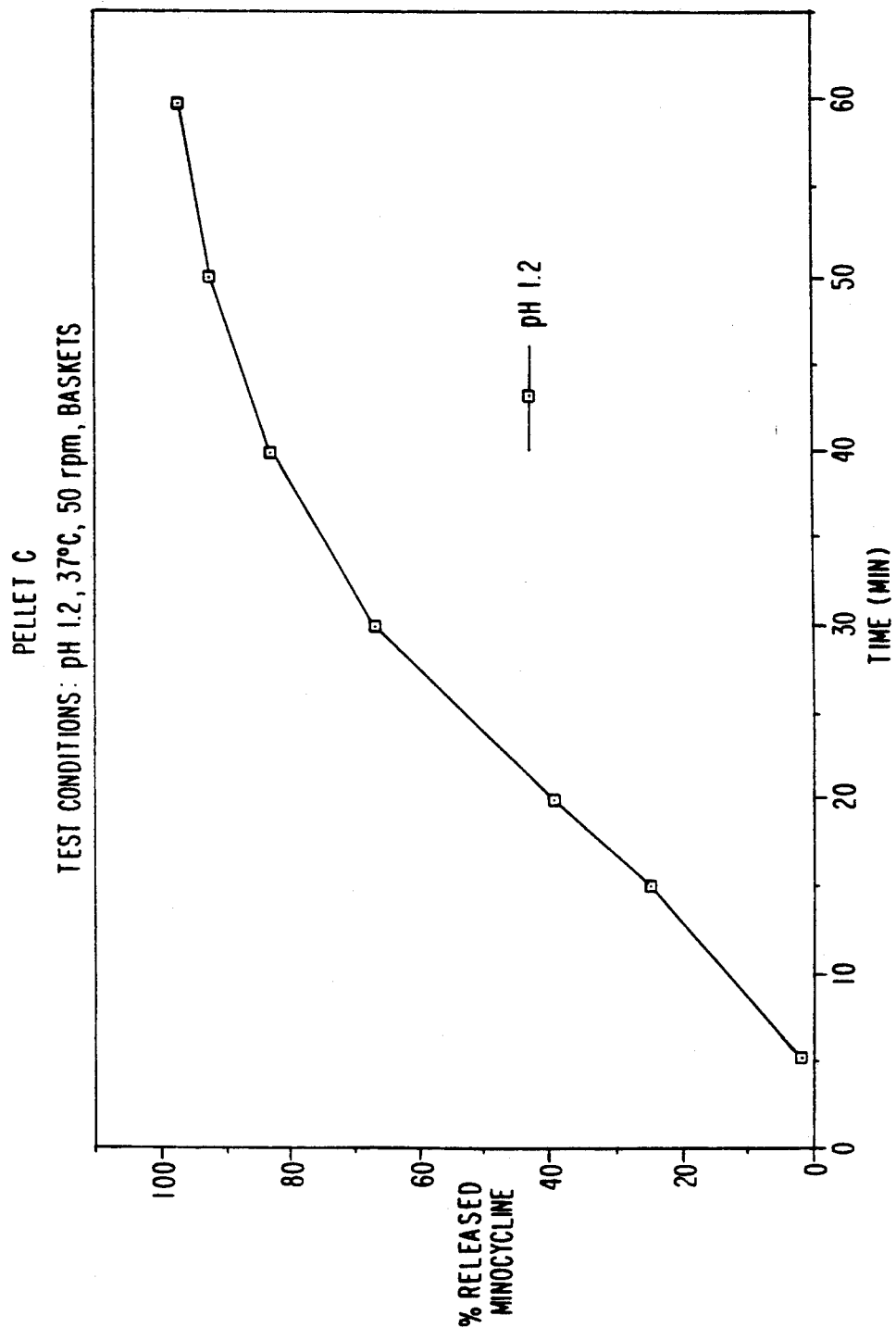

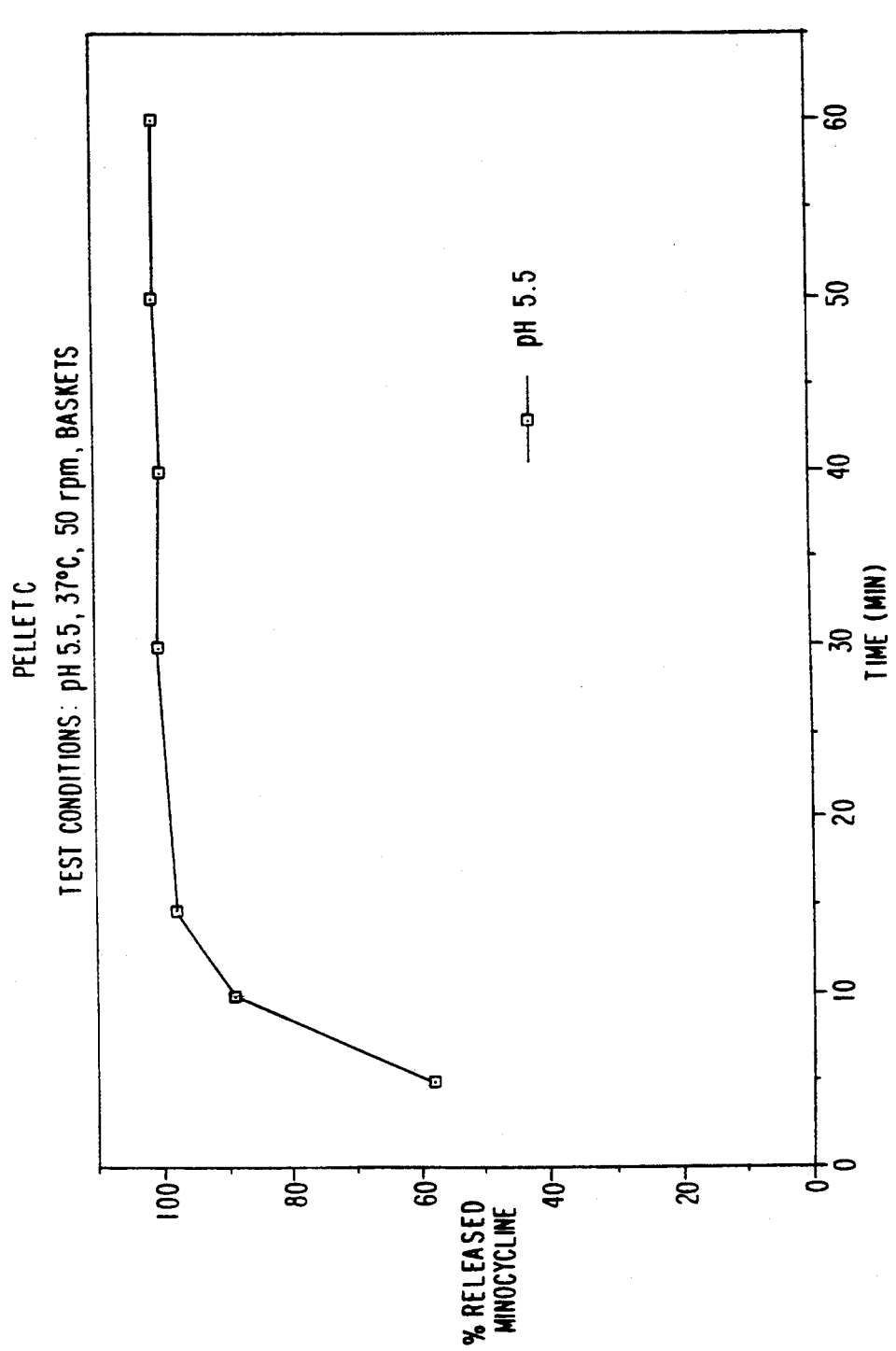

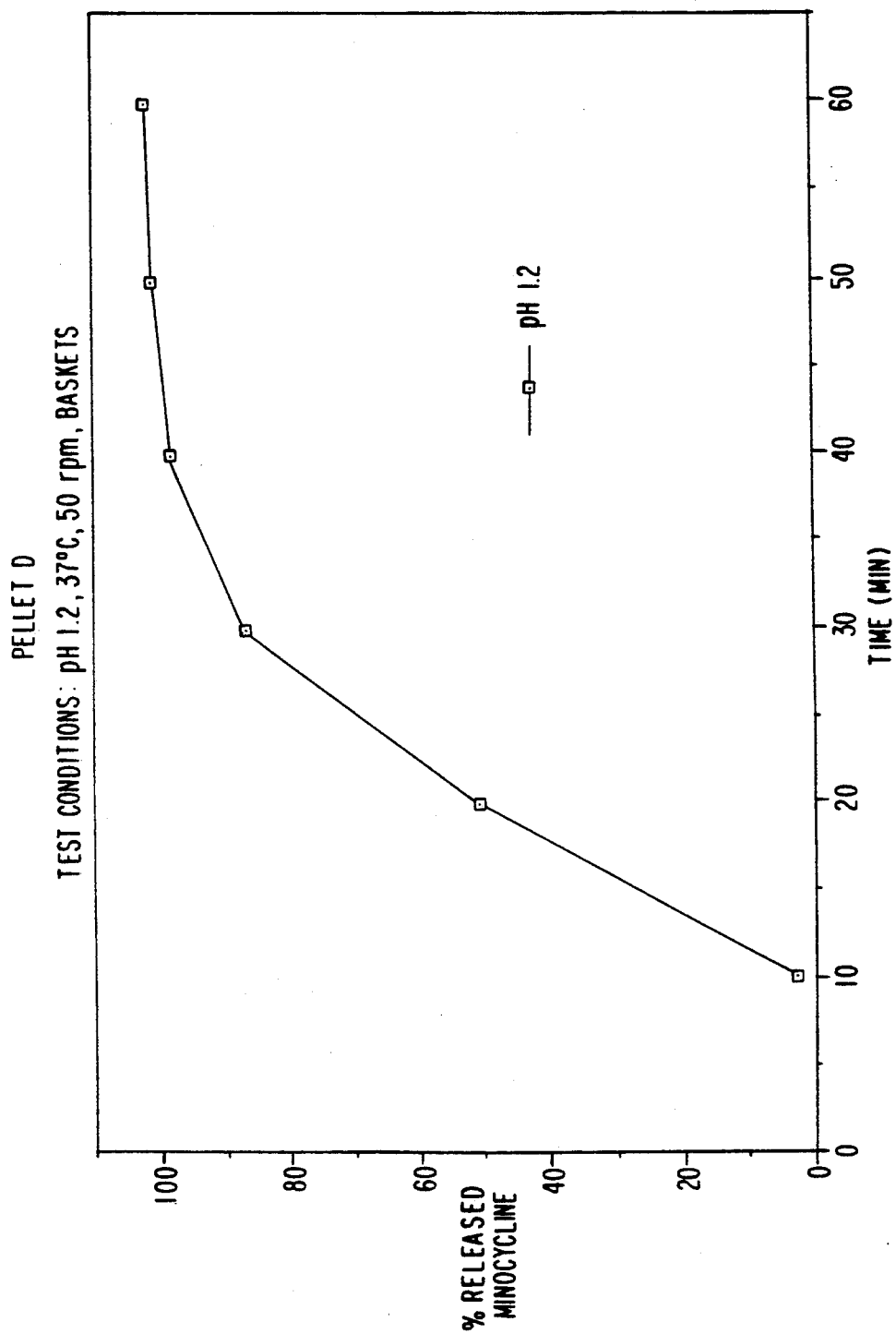

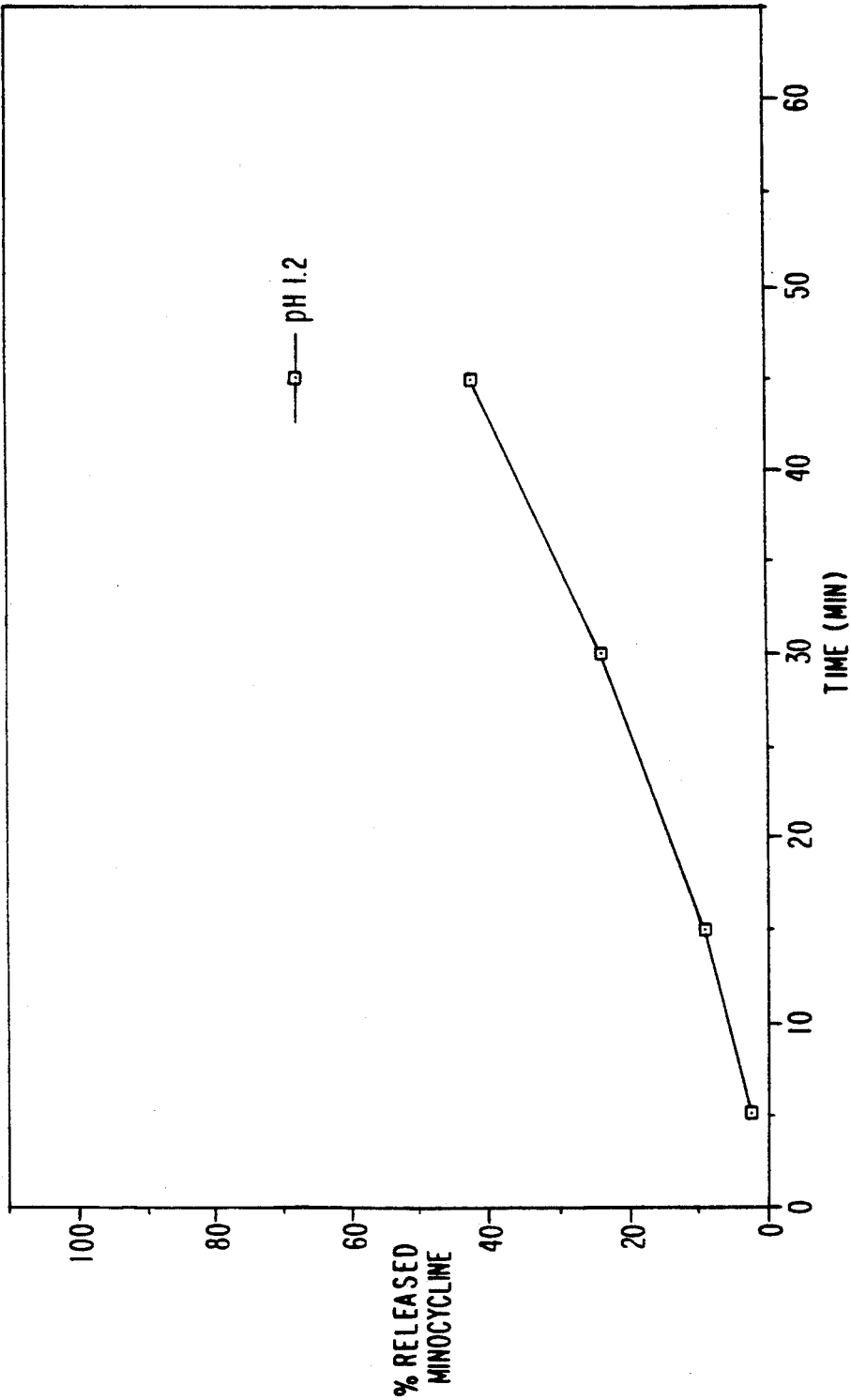

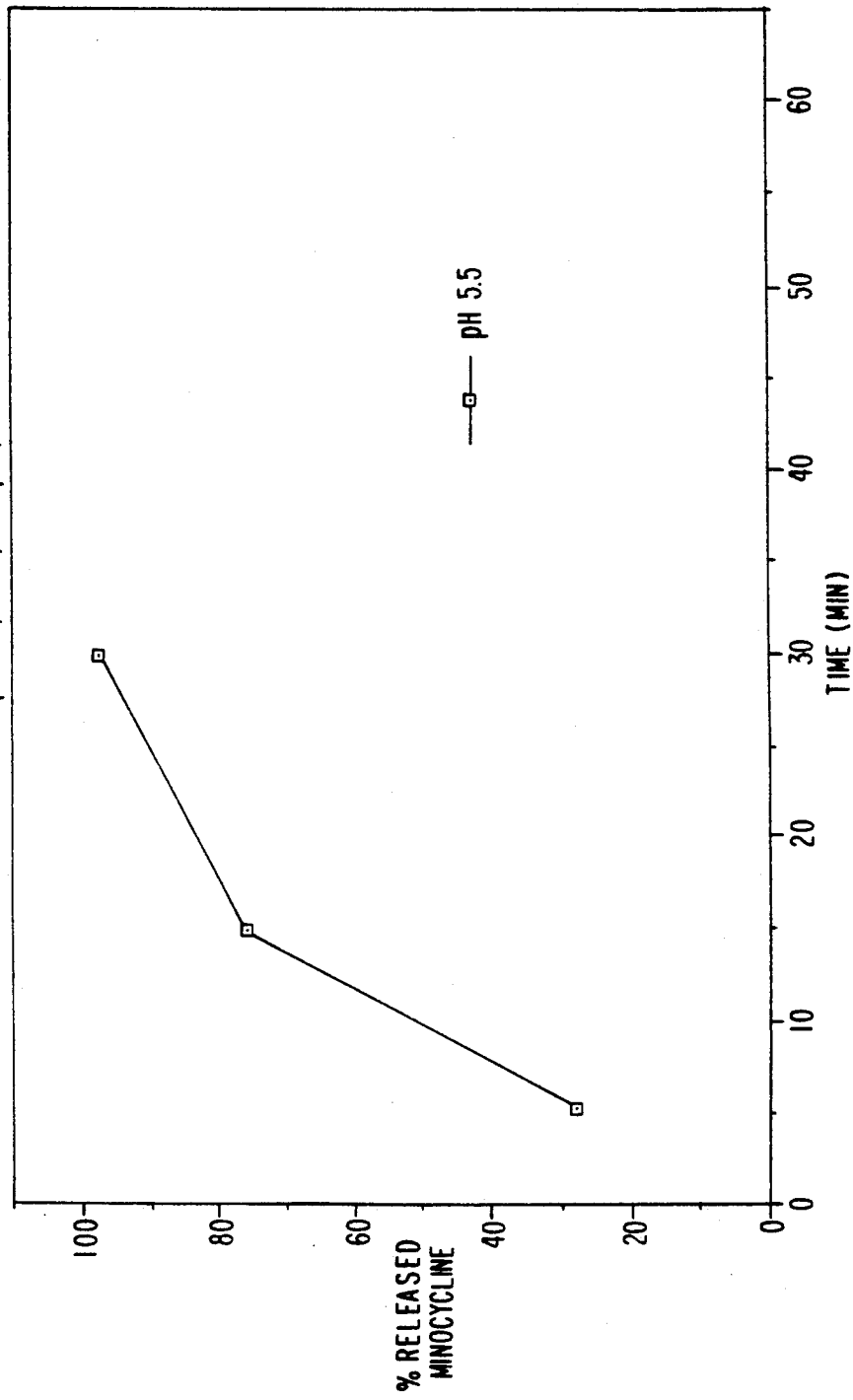

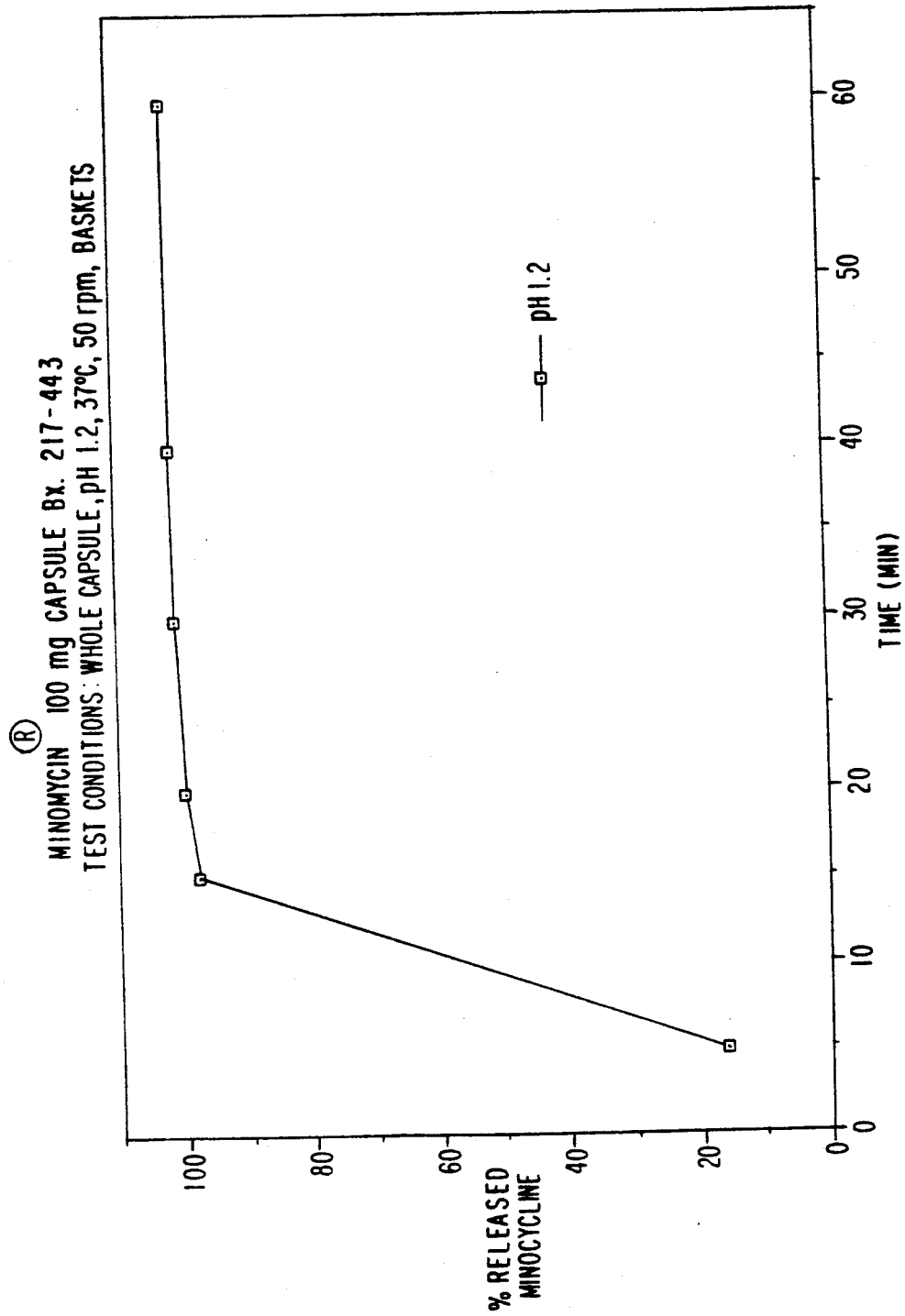

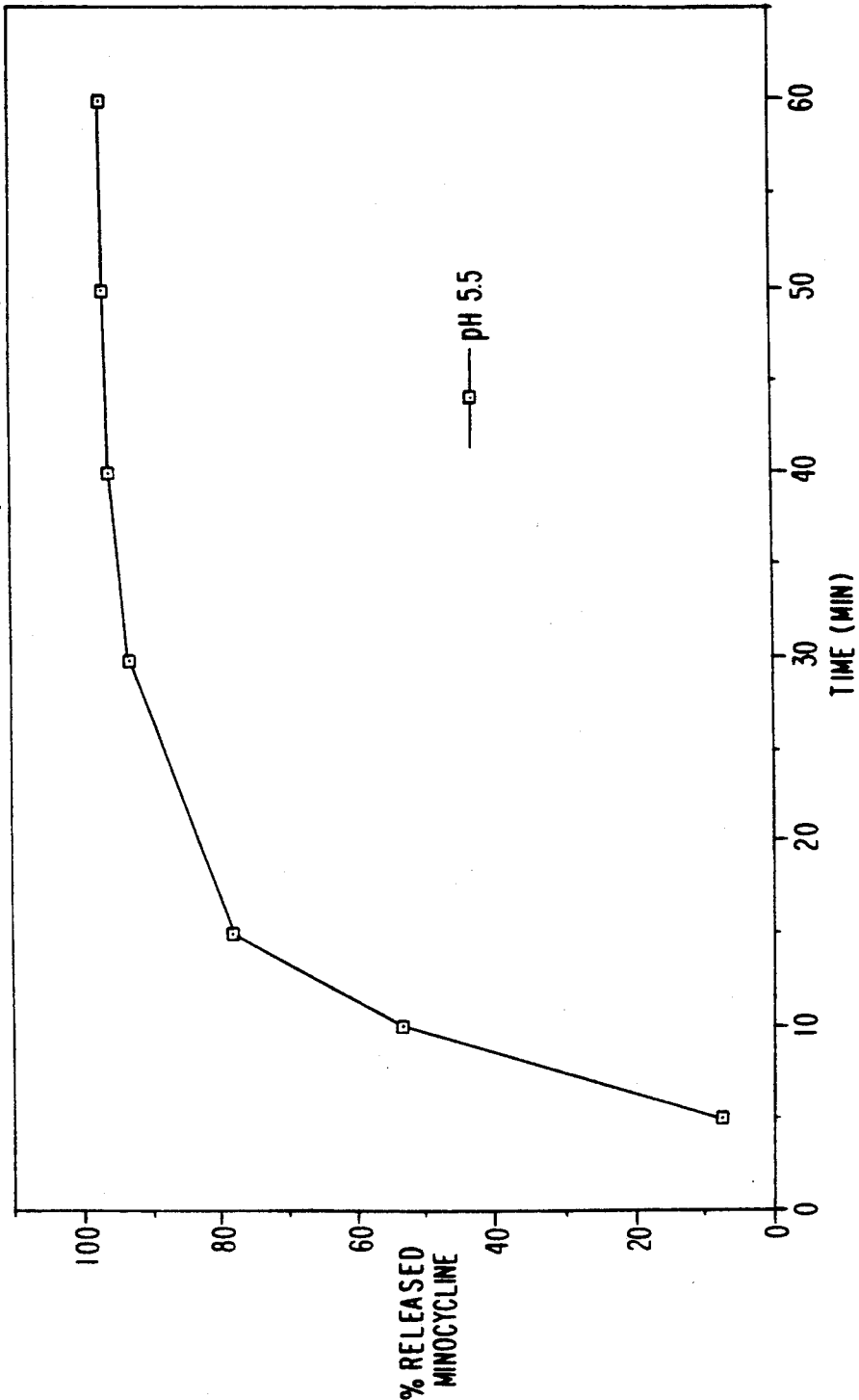

TETRACYCLINE DOSAGE FORM

The present application is a continuation-in-part of pending U.S. application, Ser. No. 304,954; filed Feb. 1, 1989, now abandoned.

FIELD OF THE INVENTION

The present invention relates to a pharmaceutical composition, in particular a pharmaceutical composition including an antibiotic agent and a method for preparing same.

BACKGROUND OF THE INVENTION

It is known in the prior art that there is a high incidence of gastrointestinal side effects associated with a number of known antibiotics including tetracycline antibiotics. These side effects include nausea and dyspepsia, particularly when taken on an empty stomach. Other side effects include reaction of the central nervous system leading to ataxia, lightheadedness, dizziness or vertigo. While it is known in the prior art to provide an enteric coating to reduce side effects by avoiding dissolution in the stomach, such enteric coatings may also prevent adequate absorption of the antibiotic. Accordingly, a product offering at least partial protection against these adverse reactions would have definite advantages over all the rest of the drug products in this group.

Accordingly, it is an object of the present invention to overcome, or at least alleviate, one or more of the difficulties related to the prior art.

Accordingly, in a first aspect according to the present invention there is provided a pharmaceutical composition including a core element including at least one active ingredient including at least one tetracycline antibiotic; and a core coating for the core element which is partially soluble at an acidic pH and which, in use, generates a dissolution profile for the pellet composition which is equal to or greater than the minimum dissolution profile required to provide bioequivalence with a capsule or tablet containing an equal amount of the at least one active ingredient in an uncoated form.

BRIEF DESCRIPTION OF THE DRAWINGS

FIG. 1. Dissolution profile for pellet composition A at pH 5.5.

FIG. 3A. Dissolution profile for pellet composition C at pH 5.5.

FIG. 3B. Dissolution profile for pellet composition C at pH 5.5.

FIG. 4A. Dissolution profile for pellet composition D at pH 5.5.

FIG. 5A. Dissolution profile for pellet composition E at pH 5.5.

FIG. 5B. Dissolution profile for pellet composition E at pH 5.5.

FIG. 6A. Dissolution profile for Minomycin ® capsules at pH 1.2.

FIG. 6B. Dissolution profile for Minomycin ® capsules at pH 5.5.

DETAILED DESCRIPTION OF THE INVENTION

Figure 2A:
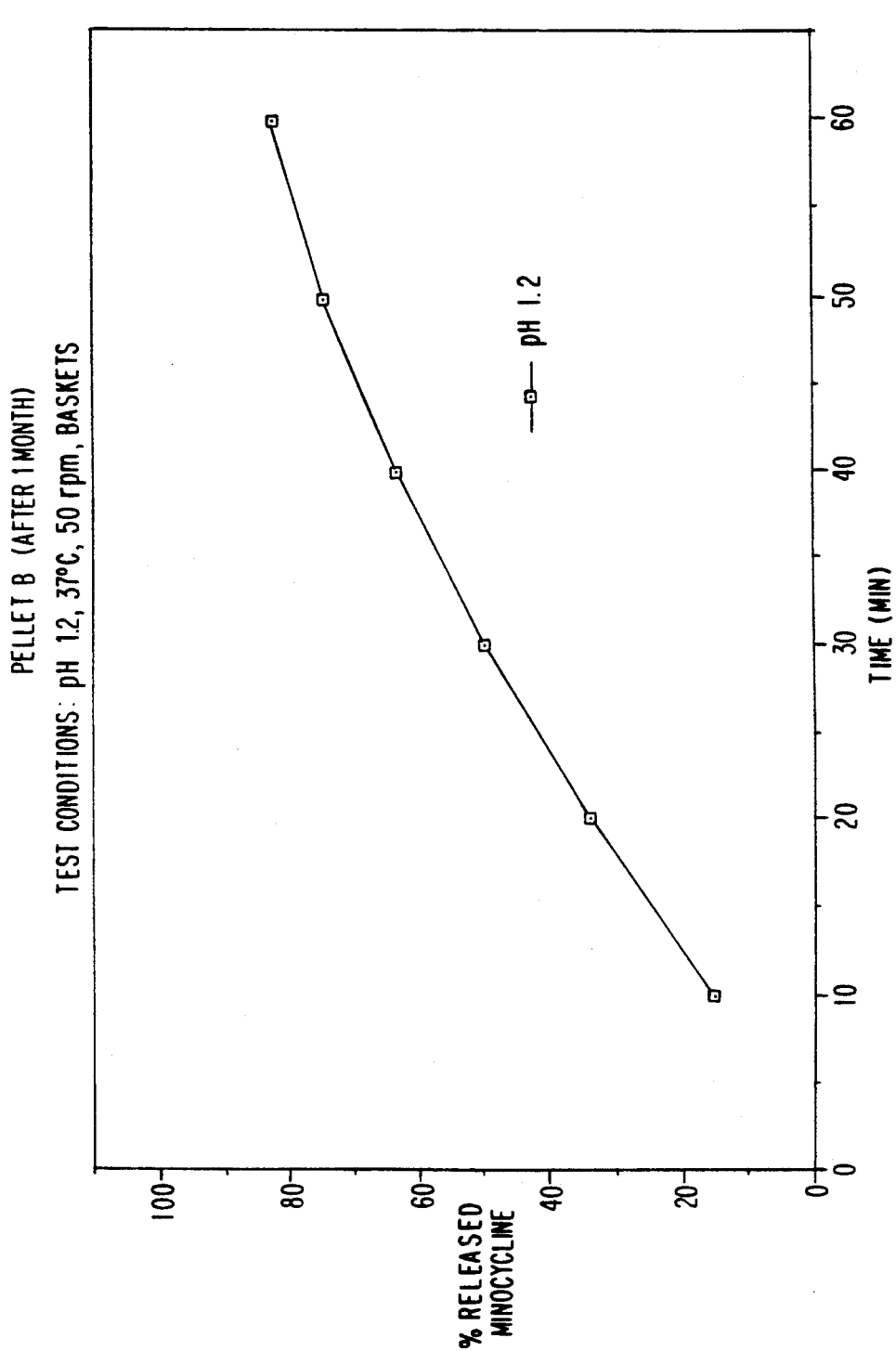
FIG. 2A. Dissolution profile for pellet composition B at pH 1.2.

A first dissolution profile may be measured at a pH level approximating that of the stomach. At least a second dissolution profile may be measured at pH levels approximating that of at least one point in the small intestine. An acidic pH may simulate the stomach and a less acidic to basic pH may simulate the small intestine.

By "acidic pH" as used herein we mean a pH in the range of approximately 1 to 4. By "less acidic to basic pH" as used herein we mean a pH in the range of approximately 4.5 to 7.5.

A pH of approximately 1.2 may be used to simulate the pH of the stomach.

A pH of approximately 5.0 to 6.0, preferably 5.5 may be used to simulate the pH at the upper end of the small intestine.

"Bio-equivalence" as used herein, means that the area under the curve (AUC) and the maximum concentration in the blood (Cmax) from a plot of blood concentration of active ingredient versus time are within certain designated requirements by Health Authorities. For example, the blood drug concentrations achieved may be plus or minus 20% in 80% or above of the subjects when compared to an immediate release product.

"Dissolution profile" as used herein, means a plot of percentage of active ingredient released as a function of time. The dissolution profile may be measured utilizing the standard test USPXXI 1985 and the 3rd and 5th Supplements (Test 711). A profile is characterized by the test conditions selected. Thus the dissolution profile may be generated at a preselected shaft speed and pH of the dissolution media.

Preferably, the pharmaceutical pellet composition generates a dissolution profile in which between 10% and 95% of the coated pellet dissolves in 30 minutes at pH 1.2 and greater than 50% of the coated pellet dissolves after 30 minutes at pH 5.5.

More preferably, the dissolution profile is preferably 20-75% dissolved in 20 minutes and/or 50% or greater dissolved in one hour at pH 1.2, and greater than 75% dissolved after 30 minutes at pH 5.5.

In order to avoid toxicity and/or other side effects, the dissolution profile at pH 1.2 should preferably not extend beyond that defined by the following table:

| Upper Dissolution Limit for Pellet Composition (pH 1.2) | |
|---|---|
| Time (Min) | % Released |
| 5 | 20 |
| 10 | 50 |
| 15 | 72 |
| 20 | 86 |
| 30 | 100 |

The pharmaceutical composition generates a dissolution profile at pH 5.5 which is faster than the dissolution profile at pH 1.2.

The pharmaceutical composition may be in a multi-pellet encapsulated form, tableted pellets or a tablet.

Accordingly, in a further aspect of the present invention there is provided a pharmaceutical product including a plurality of pellets including a core element including at least one active ingredient including at least one tetracycline antibiotic; and a core coating for the core element which is partially soluble at an acidic pH and which, in use, generates a dissolution profile for the pellet composition which is equal to or greater than the minimum dissolution profile required to provide bioequivalence with a capsule or tablet containing an equal amount of the at least one active ingredient in an uncoated form.

It will be understood that since the active ingredient in the pharmaceutical composition is released at a low rate at an acidic pH, for example, as encountered in the stomach of a patient to be treated; the side effects of antibiotics encountered in the prior art are minimized by minimizing the concentrations of antibiotic in the stomach. However, the coating and core element both dissolve at a rapid rate in a less acidic to basic environment, for example, as encountered in the upper small intestine so that effective therapeutic levels are then rapidly achieved. In this manner, the peak concentrations of tetracycline antibiotic in the blood stream of the patient are reduced while maintaining effective therapeutic levels.

Moreover, since the core coating is partially soluble at an acidic pH, for example, as encountered in the stomach of the patient, dispersion or release of active ingredients may occur rapidly once the pellet composition enters the environment of the small intestine.

The active ingredient is available for absorption even in regions of the gastrointestinal tract which are not sufficiently alkaline to rapidly dissolve the enteric core coating component.

Accordingly, in a further aspect there is provided a pharmaceutical composition including
a core element including at least one active ingredient including at least one tetracycline antibiotic; and
a core coating for the core element which is partially soluble at an acidic pH and wherein the active ingredient is available for substantially complete absorption substantially immediately after entering the small intestine.

Thus, the active ingredient is available for absorption in an absorption region substantially immediately after the pyloric sphincter in the patient. Such an absorption region may generally be characterized by a pH between approximately 1.0 and 6.0, preferably 1.2 and 5.5.

Accordingly, in a preferred aspect according to the present invention there is provided
a pharmaceutical composition including
including at least one active ingredient including at least one tetracycline antibiotic; and
a hybrid core coating which coating provides a controlled low rate of release at an acidic pH and is soluble at a rapid rate at a less acidic to basic pH.

The hybrid core coating may include
at least one polymer which is substantially insoluble at acidic pH and at least partially soluble at a less acidic to basic pH; and
at least one component which is at least partially soluble at acidic pH.

The rate of dissolution of the hybrid core coating will depend on the amounts of the at least one partially soluble component, the at least one polymer which is substantially insoluble at an acidic pH, and the thickness of the coating. Typical core coatings may be in the range of approximately 5 to 200 um, preferably approximately 25 um. It will be understood, accordingly, that the rate of absorption may be modified by modifying the thickness and/or the composition of the hybrid core coating.

Once a minimum amount of the components and permeable component and the maximum thickness of the coating to achieve the minimum dissolution profile has been established, then it is simply a matter of design choice to adjust the composition and/or thickness of coating as desired.

The pharmaceutical composition according to the present invention may include a plurality of coated core elements. The pharmaceutical composition is preferably in a pellet form.

The pharmaceutical composition may be provided in any suitable unit dosage form. An encapsulated form or tableted pellets may be used. The encapsulated pharmaceutical pellet composition may thus provide, in use, a blood profile in a patient to be treated which is substantially bio-equivalent to commercial capsules or tablets including the active ingredient in an uncoated form.

While we do not wish to be restricted by theory, it is postulated that the pharmaceutical composition according to the present invention does not increase the risk of gastric mucosal membrane ulceration relative to conventional tablets or capsules, mainly because of the low concentration of dissolved drug at any point in the gastrointestinal tract at any one time. The pellets, when released from the dosage form by dissolution of the capsule shell (capsules) or disintegration of the tablet (tablets) disperse throughout the gastrointestinal tract as they are releasing drug. Consequently, the pelletized dosage forms do not produce the high localized concentration of active drug which could be expected from conventional tablets or capsules.

The pharmaceutical composition according to the first aspect of the present invention includes a core element as stated above. The active ingredient in the core element includes at least one tetracycline antibiotic. The tetracycline antibiotic may be selected from tetracycline, chlortetracycline, demeclocyline, methocycline, oxytetracycline and minocycline. Minocycline is preferred. Mixtures of one or more of the above antibiotic agents with minocycline may be used.

In a preferred aspect the core element of the pharmaceutical composition according to the present invention may include an effective amount of
at least one tetracycline antibiotic;
at least one core seed; and
at least one binding agent.

Such a core element is preferred where a pharmaceutical pellet composition is to be formed, e.g., utilizing a spheronization process.

In an alternative form, the core element of pharmaceutical composition according to the present invention may include an effective amount of
at least one tetracycline antibiotic;
at least one binding agent; and
at least one filler.

Such a core element is preferred where a pharmaceutical pellet composition is to be formed, e.g., utilizing an extrusion process.

In a still further alternative form, where the pharmaceutical composition takes the form of a coated tablet, the core element may take the form of a tablet. Accordingly, the core element may include
at least one tetracycline antibiotic;
at least one lubricant; and
at least one filler.

The core element according to this embodiment may further include at least one disintegrant.

The at least one tetracycline antibiotic may be present in any suitable effective amount. The tetracycline antibiotic may be present in amounts of approximately 5 to 95% by weight, preferably approximately 20 to 75% by weight, based on the total weight of the core element. The binding agent may be present in amounts of from approximately 0 to 45%, preferably 0.1 to 20% by weight based on the total weight of the core element.

The binding agent may be of any suitable type. Suitable binders may be selected from polyvinylpyrrolidone (povidone), hydroxypropyl cellulose, hydroxypropyl methylcellulose, methylcellulose and hydroxyethyl cellulose, sugars and mixtures thereof. The binding agent may be provided in the form of a granulating solution. An aqueous or organic solvent may be included. Methanol, ethanol or mixtures thereof may be used as solvents.

The core seed, when present, may be present in any suitable effective amount. The size and amount of the core seed may vary substantially depending upon the amount of active ingredient to be included. Accordingly, the core seeds may vary from approximately 5.0 to 95% by weight, preferably 25 to 80% by weight based on the total weight of the core element. The core seed may be of such a diameter to provide a final core element having a diameter of approximately 500 to 2000 um.

The core seed may be of any suitable type. A sugar sphere may be used.

Suitable fillers may be selected from insoluble materials such as silicon dioxide, talc, alumina, starch, kaolin, polacrilin potassium, powdered cellulose, and microcrystalline cellulose and mixtures thereof. Soluble fillers may be selected from mannitol, sucrose, lactose, dextrose, sodium chloride, sorbitol and mixtures thereof. Lactose and/or starch fillers are prepared where the core element is in a tablet form.

The lubricant and disintegrant, where present, may be selected from any of these known per se in the formulation of tablets. As lubricant, talc, magnesium stearate or stearic acid may be used. As disintegrant, microcrystalline cellulose or polacrilin potassium may be used.

In a further preferred aspect, the core element according to this aspect of the present invention may further include other carriers or excipients, stabilizing agents, solution accelerants, and colorants.

A solution accelerator may be included. A polyethylene glycol may be used as a solution accelerator. The preferred polyethylene glycol used may be selected from polyethylene glycol 4000 and polyethylene glycol 6000.

The filler may be present in amounts of from approximately 0 to 75% by weight, preferably 1 to 40% by weight, based on the total weight of the core element. The polyethylene glycol component when present may be present in amounts of from approximately 1 to 50% by weight based on the total weight of the core element.

Typical core formulations may be prepared in the amounts as follows:

| Spheronization Process | | |
|---|---|---|
| Example A | | |
| (antibiotic) | minocycline powder | 20-74% |
| | sugar seeds | 25-80% |
| (binder) | hydroxypropyl methylcellulose (as hydroxypropyl methylcellulose/methanol granulating solution) | 0.1-20% |
| Example B | | |
| (antibiotic) | minocycline powder | 20-74% |
| | sugar seeds | 25-80% |
| (binder) | povidone (as povidone/ethanol granulating solution) | 0.1-20% |
| Extrusion process | | |
| (antibiotic) | minocycline powder | 20-74% |
| (filler) | microcrystalline cellulose | 1-75% |
| (binder) | hydroxypropyl cellulose | 1-10% |
| (solvent) | water | sufficient for extrusion |
| Tablet Form | | |
| (antibiotic) | minocycline powder | 20-74% |
| (filler) | lactose | 1-40% |
| (lubricant) | talc | 1-40% |
| (disintegrant) | microcrystalline cellulose | 1-75% |

The pharmaceutical composition according to this aspect of the present invention further includes a hybrid core coating. It will be understood that the hybrid core coating reduces but does not eliminate dissolution in the acidic environment of the stomach but will allow rapid dissolution in the environment of the upper intestinal tract.

The enteric polymer, while substantially insoluble at acidic pH may dissolve rapidly in the less acidic to basic pH encountered in the small intestine.

The at least partially acid soluble component may dissolve rapidly in the acid environment of the stomach.

Preferably, the hybrid core coating includes approximately 15 to 85% by weight, based on the total weight of the hybrid core coating, excluding filler, of at least one acid insoluble polymer and may be selected from the enteric polymers cellulose acetate phthalate, hydroxypropyl methycellulose phthalate, polyvinyl acetate phthalate, methacrylic acid copolymer type A, methacrylic acid : acrylic acid methyl ester copolymer, hydroxypropyl methylcellulose acetate succinate, shellac, cellulose acetate trimellitate or mixtures thereof; and approximately 1 to 60% by weight, based on the total weight of the hybrid core coating, excluding filler, of an at least partially acid soluble component selected from polyvinylpyrrolidone, hydroxypropyl cellulose, hydroxypropyl methylcellulose, methylcellulose, sugars and mixtures thereof.

The hybrid core coating may further include
at least one plasticizer;
and optionally
at least one filler.

The at least one plasticizer may be selected from diethyl phthalate, triethyl citrate, triethyl acetyl citrate, triacetin, tributyl citrate, polyethylene glycol, glycerol and the like. It will be understood that the plasticizer used may be largely dictated by the polymer used in the coating formulation.

The plasticizer may be present in any suitable effective amount. Amounts of from 0 to approximately 50% by weight, preferably 1-30% by weight, based on the total weight of the hybrid core coating have been found to be suitable.

It should be noted that plasticizers which are significantly water soluble may behave as a partially acid soluble component in the hybrid core coating.

A preferred hybrid core coating includes

| (enteric polymer) | hydroxypropyl methyl cellulose phthalate | 50-80% |
|---|---|---|
| (acid-soluble polymer) | polyvinylpyrrolidone | 10-40% |

| | |
|---|---|
| -continued | |
| (plasticizer) triethyl citrate | 1-30% |

As stated above, the hybrid core coating may further include at least one filler. The at least one filler may be selected from those insoluble fillers listed above for the manufacture of the core element.

The filler may be present in any suitable effective amount. Amounts of from 0 to approximately 75% by weight, preferably 0–50% by weight based on the total weight of the core coating have been found to be suitable.

A hybrid core coating composition may be provided in the form of a solution, dispersion or suspension.

The solvent may be present in amounts of from approximately 25 to 97% by weight based on the total weight of the hybrid core coating composition. The solvent for the enteric polymer may be an aqueous solvent. The solvent for the enteric polymer may be selected from water, methanol, ethanol, methylene chloride and mixtures thereof.

Typical percentage compositions of hybrid core coatings for polymers and plasticizer (following evaporation of the solvent) are:

| | % coat weight |
|---|---|
| A. insoluble at pH 1.2 (enteric) | 30–80 |
| acid soluble | 10–60 |
| plasticizer | 1–30 |
| solvent | 85–87% |
| of hybrid core coating solution | |
| B. For aqueous redispersion polymers of an enteric nature, formulation A above becomes: | |
| insoluble polymer at pH 1.2 (enteric) | 30–80 |
| acid soluble | 10–60 |
| plasticizer | 1–30 |
| solvent (water) is | 75–97% |
| of the hybrid core coating solution | |

Sufficient plasticizer is added to ensure film formation.

In a further aspect of the present invention there is provided a method for preparing a core element which method includes
  providing an active ingredient including
    at least one tetracycline antibiotic;
    at least one core seed; and
    at least one binding agent; and
  coating the core seeds with the active ingredient and binding agent.

In a preferred form the at least one binding agent is provided in a granulating solution. In this form the coating step may be conducted as a spheronization process. The spheronization process includes contacting the core seeds with the active ingredient and simultaneously adding the granulating solution thereto. The spheronization process may be conducted in a spheronizing machine.

In an alternative aspect of the present invention the method according to the present invention may further include providing the active ingredient and binder in a solution or slurry of a solvent and spraying the core seeds with the solution or slurry. The spraying step may be conducted in a fluidized bed chamber.

In a further alternative aspect of the present invention, the method for preparing a core element may include providing
  at least one tetracycline antibiotic;
  at least one binding agent; and
  an effective amount of a solvent;
  mixing the ingredients;
  and subjecting the ingredients to an extrusion step, followed by marumerization in a marumerizer.

The solvent may be an aqueous or organic solvent or mixtures thereof. The solvent may be present in an amount effective to allow the ingredients to be extruded.

The core elements formed may then be subjected to a drying step. The drying step may be conducted in a fluidized bed or drying oven.

In a still further aspect of the present invention there is provided a method for preparing a pharmaceutical pellet composition as described above which method includes
  providing a hybrid core coating composition including a solution or dispersion of
    at least one polymer which is substantially insoluble at an acidic pH but at least partially soluble at a less acidic to basic pH; and
    at least one component which is at least partially soluble at an acidic pH;
  providing a fluidized bed reactor;
  introducing the core elements into the fluidized bed reactor; and
  spray coating the core elements with the hybrid core coating composition.

Spray coating of pellets may be undertaken utilizing bottom or top located spray nozzles. A bottom spray nozzle may reside proximate the base of the fluidizing bed facing upwards while a top spraying nozzle is located above the contents of the bed and facing downward.

In a still further alternative aspect of the present invention, the method for preparing a core element may including providing
  at least one tetracycline antibiotic;
  at least one lubricant;
  at least one filler; and
  at least one disintegrant;
  mixing the ingredients; and
  subjecting the ingredients to a direct compression step.

In a still further aspect of the present invention, there is provided a method for preparing a coated tablet as described above, which method includes
  providing a hybrid core coating composition, including a solution or dispersion of
    at least one polymer which is substantially insoluble at an acidic pH but at least partially soluble at a less acidic pH;
    at least one component which is at least partially soluble at an acidic pH;
  and a pan coater;
  introducing the tablets into the pan coater; and
  spraying or pouring the hybrid core coating into the pan to coat the tablets.

Preferably, the final hybrid core coating, including filler, is about 5% to about 20% weight of the core, most preferably, it is about 7% to about 14% by weight.

The pharmaceutical pellet or tablet composition may be administered under a similar dosage regimen to that used in the prior art. For minocycline, for example, the multi-pellet encapsulated or tablet form may be administered at the same frequency as commercially available forms such as that sold under the trade designation Minomycin, e.g., 200 mg followed by 100 mg every 12 hours.

In accordance with a further aspect of the present invention there is provided a method of treating bacterial infections in patients requiring such treatment which method includes administering to a patient an effective amount of a pharmaceutical pellet composition as described above.

It will be understood that the method of treating bacterial infections according to this aspect of the present invention may provide an advantage in reduced side effects associated with prior art antibiotics as described above. These side effects include nausea, dyspepsia and central nervous system irregularities.

The present invention will now be more fully described with reference to the accompanying examples. It should be understood, however, that the following description is illustrative only and should not be taken in any way as a restriction on the generality of the invention specified above.

EXAMPLE 1

Pellet compositions A-E having the formulations set out below were prepared as described below.

A
Core Composition
Non pareil seed cores: 150 mg
Minocycline hydrochloride: 123 mg
Povidone USP: 20 mg
Hybrid Core Coating Composition
Hydroxypropyl methylcellulose phthalate: 30 mg
Diethyl phthalate: 2.5 mg

B
Core Composition
Non pareil seed cores: 150 mg
Minocycline hydrochloride: 123 mg
Povidone USP: 20 mg
Hybrid Core Coating Composition
Hydroxypropyl methylcellulose phthalate: 6 mg
Diethyl phthalate: 1.5 mg
Hydroxypropyl methylcellulose: 1.5 mg

C
Core Composition
Non pareil seed cores: 150 mg
Minocycline hydrochloride: 164 mg
Povidone USP: 20 mg
Hybrid Core Coating Composition
Hydroxypropyl methylcellulose phthalate: 19.0 mg
Providone USP: 7.0 mg
Triethyl citrate: 2.5 mg
Talc: 14.5 mg

D
Core Composition
Non pareil seed cores: 150 mg
Minocycline hydrochloride: 125 mg
Povidone USP: 18 mg
Hybrid Core Coating Composition
Hydroxypropyl methylcellulose phthalate: 19.5 mg
Hydroxypropyl methylcellulose: 10.4 mg
Triethyl citrate: 2.6 mg
Kaolin:* 32.5 mg

E
Core Composition
Non pareil seed cores: 150 mg
Minocycline hydrochloride: 138 mg
Povidone USP: 19 mg
Hybrid Core Coating Composition
Hydroxypropyl methylcellulose phthalate: 21.7 mg
Sorbitol: 19.1 mg
Polyoxyl 40 stearate: 0.7 mg
Triethyl citrate: 2.7 mg -continued
Talc: 21.0 mg

*Added to coating solution prior to application of the coating to the core.

The sugar seeds were placed in a spheronizer and coated with a dry mixture of the active ingredients and inactive excipients while concomitantly adding a solution of the binder components.

The wet cores so formed were then placed in a fluidized bed dryer for 1 hour and placed in a bottom spray coating fluidized bed apparatus. The hybrid core coating composition was then delivered into the fluidized bed via the bottom spraying nozzle.

The wet pellets so formed were then allowed to dry.

EXAMPLE 2

A dissolution test was conducted on the pellet compositions A-E and on commercial tetracycline capsules, for comparison purposes, utilizing the test method USPXXI 1985 and the 3rd and 5th Supplement thereto (Test 711). The commercial tetracycline capsules incorporated minocycline powders and were sold under the trade designation "Minomycin". A sample is dissolved in an aqueous medium previously degassed and equilibrated to 37° C. The media are USP pH 1.2 media without enzymes or pH 5.5 phthalate buffer. A sample of known volume is withdrawn at designated time intervals from the bath as directed and subjected to a suitable assay procedure. The mg of minocycline released as a function of time is plotted as the dissolution profile.

The tests were conducted at pH 1.2 and pH 5.5.

The baskets containing the samples were rotated at approximately 50 rpm and the aqueous medium maintained at approximately 37° C.

Figure 2B:
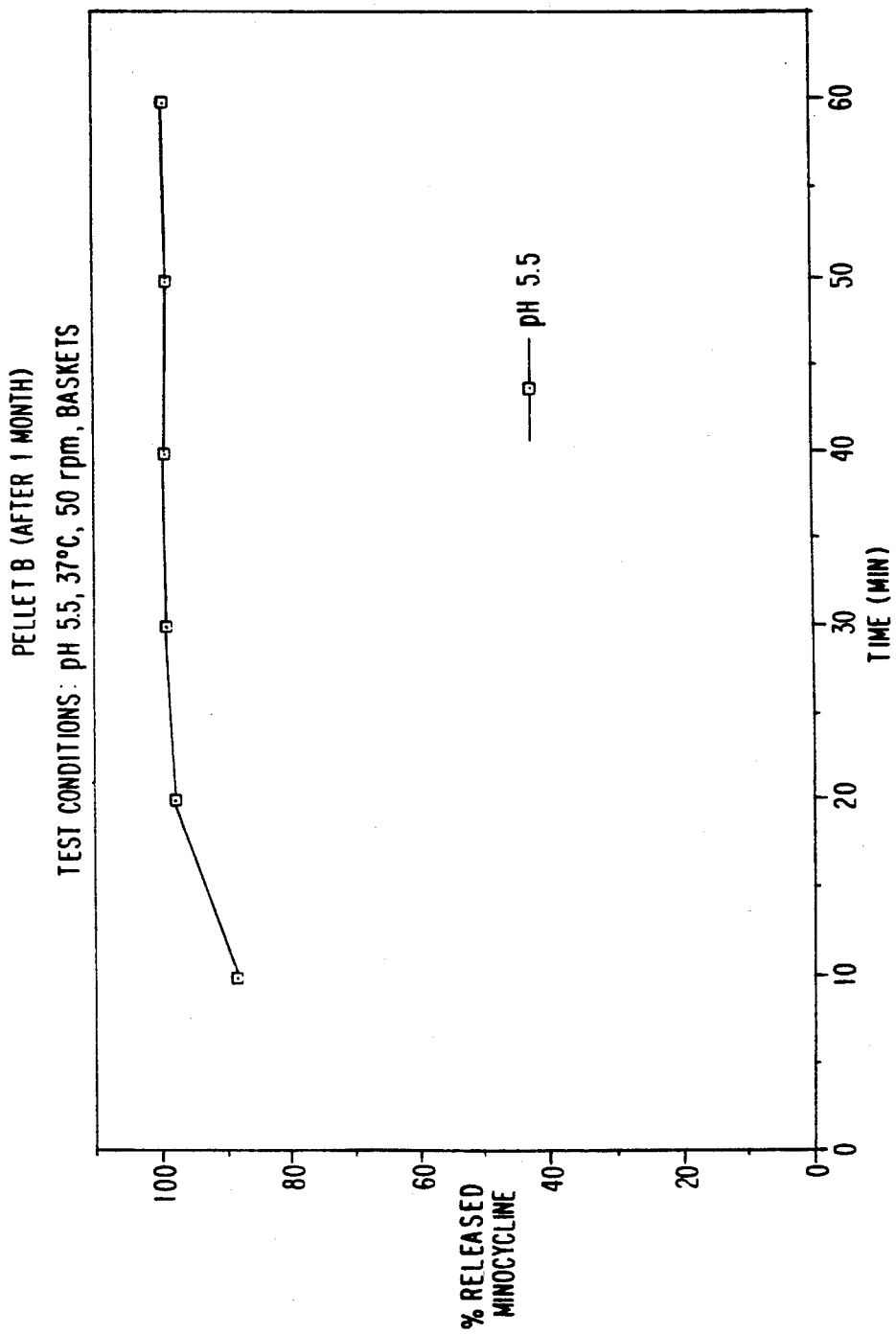
FIG. 2B. Dissolution profile for pellet composition B at pH 5.5.
Figure 4B:
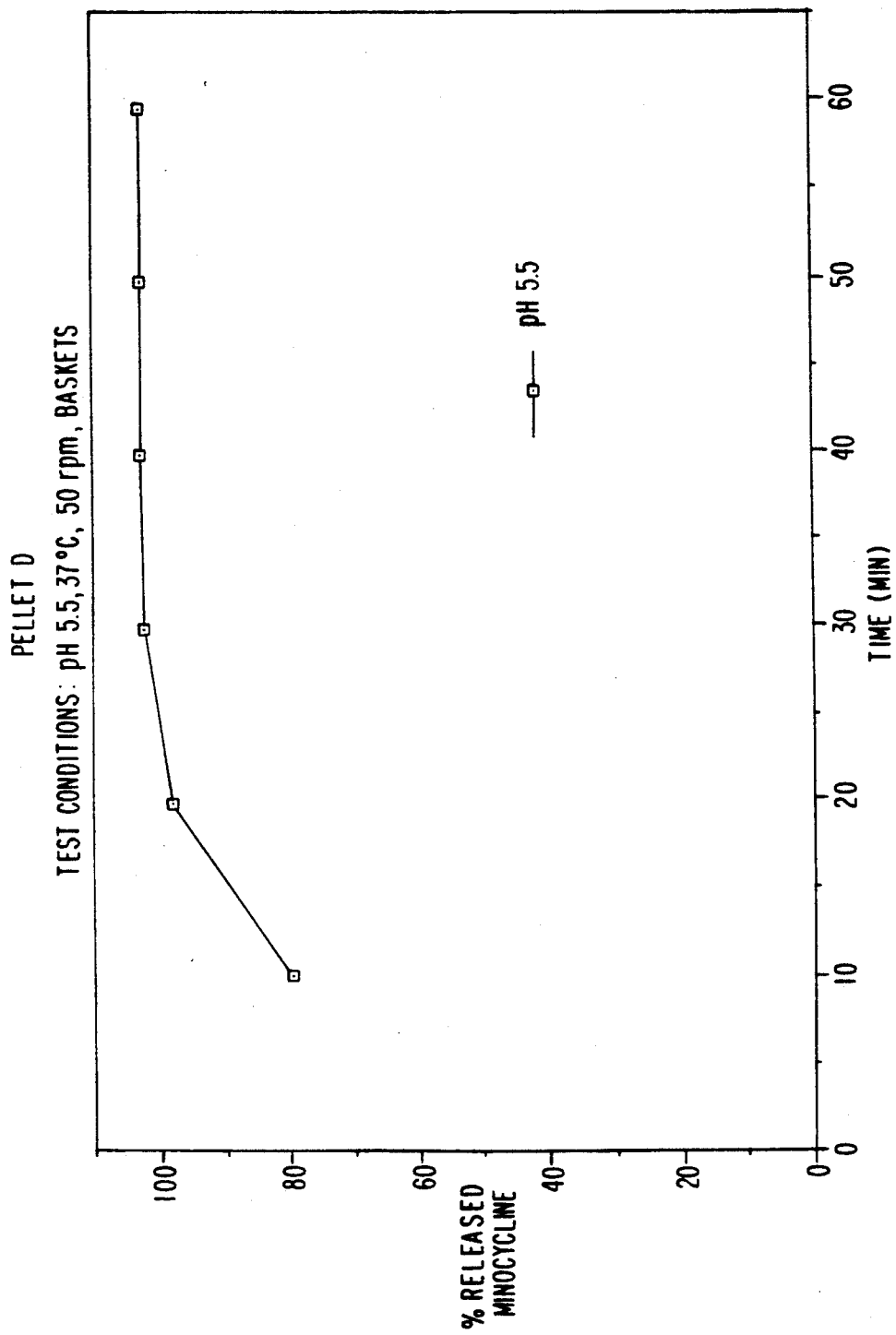
FIG. 4B. Dissolution profile for pellet composition C at pH 5.5.

The results are given in Tables 1–11. For compositions A and B and for Minomycin ®, the results are shown in FIGS. 1–3. The hybrid coating on pellet composition A functioned as an enteric coating and no dissolution at pH 1.2 was observed over a 1 hour period.

TABLE 1

DISSOLUTION DATA FOR PELLET COMPOSITION B MEASURED AT pH 5.5
(Averaged data for 3 samples)

| TIME (Min) | AMOUNT RELEASED (mg) | STD DEV | % RELEASED | STD DEV |
|---|---|---|---|---|
| 10 | 27.18 | (1.07) | 82.17 | (4.06) |
| 20 | 32.79 | (0.63) | 99.12 | (0.38) |
| 30 | 33.35 | (1.02) | 100.78 | (1.49) |
| 40 | 33.29 | (1.06) | 100.61 | (1.56) |

TABLE 2

DISSOLUTION DATA FOR PELLET COMPOSITION B MEASURED AT pH 1.2
(Averaged data for 3 samples)

| TIME (Min) | AMOUNT RELEASED (mg) | STD DEV | % RELEASED | STD DEV |
|---|---|---|---|---|
| 10 | 7.97 | (0.32) | 15.60 | (0.64) |
| 20 | 17.78 | (0.75) | 34.71 | (1.62) |
| 30 | 26.17 | (0.89) | 51.23 | (2.15) |
| 40 | 33.10 | (1.10) | 64.79 | (2.66) |
| 50 | 38.65 | (1.23) | 75.67 | (3.09) |
| 60 | 42.45 | (1.24) | 83.09 | (3.13) |

TABLE 3

DISSOLUTION DATA FOR PELLET COMPOSITION B MEASURED AT pH 5.5
(Averaged data for 3 samples)

| TIME (Min) | AMOUNT RELEASED (mg) | STD DEV | % RELEASED | STD DEV |
|---|---|---|---|---|
| 10 | 45.27 | (2.30) | 88.60 | (4.87) |
| 20 | 50.25 | (0.49) | 98.33 | (1.66) |
| 30 | 50.91 | (0.17) | 99.64 | (1.01) |
| 40 | 51.02 | (0.05) | 99.85 | (0.93) |
| 50 | 50.89 | (0.21) | 99.58 | (1.03) |
| 60 | 51.00 | (0.31) | 99.80 | (1.08) |

TABLE 4

DISSOLUTION DATA FOR PELLET COMPOSITION C MEASURED AT pH 1.2
(Averaged data for 3 samples)

| TIME (Min) | AMOUNT RELEASED (mg) | STD DEV | % RELEASED | STD DEV |
|---|---|---|---|---|
| 5 | 0.80 | (0.00) | 1.64 | (0.00) |
| 15 | 12.06 | (1.10) | 24.81 | (2.25) |
| 20 | 19.21 | (0.65) | 39.54 | (1.35) |
| 30 | 32.53 | (1.04) | 66.95 | (2.14) |
| 40 | 40.31 | (1.33) | 82.97 | (2.79) |
| 50 | 44.91 | (1.21) | 92.42 | (2.57) |
| 60 | 47.28 | (1.13) | 97.30 | (2.40) |

TABLE 5

DISSOLUTION DATA FOR PELLET COMPOSITION C MEASURED AT pH 5.5
(Averaged data for 3 samples)

| TIME (Min) | AMOUNT RELEASED (mg) | STD DEV | % RELEASED | STD DEV |
|---|---|---|---|---|
| 5 | 28.99 | (1.85) | 59.09 | (4.50) |
| 10 | 44.23 | (1.16) | 90.08 | (1.94) |
| 15 | 48.62 | (1.23) | 99.01 | (0.99) |
| 30 | 49.95 | (0.88) | 101.73 | (0.68) |
| 40 | 49.82 | (0.95) | 101.46 | (0.62) |
| 50 | 50.30 | (0.60) | 102.45 | (0.46) |
| 60 | 50.24 | (0.69) | 102.31 | (0.31) |

TABLE 6

DISSOLUTION DATA FOR PELLET COMPOSITION D MEASURED AT pH 1.2
(Averaged data for 3 samples)

| TIME (Min) | AMOUNT RELEASED (mg) | STD DEV | % RELEASED | STD DEV |
|---|---|---|---|---|
| 10 | 1.13 | (0.10) | 3.01 | (0.30) |
| 20 | 19.36 | (0.43) | 51.81 | (1.62) |
| 30 | 32.87 | (1.02) | 87.95 | (2.11) |
| 40 | 37.05 | (1.93) | 99.09 | (1.31) |
| 50 | 38.17 | (2.16) | 102.05 | (1.26) |
| 60 | 38.54 | (2.32) | 103.04 | (1.33) |

TABLE 7

DISSOLUTION DATA FOR PELLET COMPOSITION D MEASURED AT pH 5.5
(Averaged data for 3 samples)

| TIME (Min) | AMOUNT RELEASED (mg) | STD DEV | % RELEASED | STD DEV |
|---|---|---|---|---|
| 10 | 43.54 | (0.72) | 79.81 | (1.15) |
| 20 | 53.52 | (0.46) | 98.11 | (1.15) |
| 30 | 55.75 | (1.03) | 102.20 | (2.20) |
| 40 | 56.14 | (1.13) | 102.91 | (2.40) |
| 50 | 56.11 | (1.23) | 102.86 | (2.55) |
| 60 | 56.16 | (1.11) | 102.96 | (2.35) |

TABLE 8

DISSOLUTION DATA FOR PELLET COMPOSITION E MEASURED AT pH 1.2
(Averaged data for 3 samples)

| TIME (Min) | AMOUNT RELEASED (mg) | STD DEV | % RELEASED | STD DEV |
|---|---|---|---|---|
| 05 | 1.31 | (0.27) | 2.38 | (0.46) |
| 15 | 5.07 | (0.32) | 9.20 | (0.46) |
| 30 | 13.44 | (0.85) | 24.39 | (1.25) |
| 45 | 23.76 | (1.58) | 43.13 | (2.33) |

TABLE 9

DISSOLUTION DATA FOR PELLET COMPOSITION E MEASURED AT pH 5.5
(Averaged data for 3 samples)

| TIME (Min) | AMOUNT RELEASED (mg) | STD DEV | % RELEASED | STD DEV |
|---|---|---|---|---|
| 05 | 15.42 | (2.33) | 27.77 | (4.42) |
| 15 | 42.17 | (1.64) | 75.89 | (3.78) |
| 30 | 53.98 | (0.30) | 97.13 | (1.66) |

TABLE 10

DISSOLUTION DATA FOR Minomycin ®, i.e, MINOCYCLINE POWDER CAPSULES MEASURED AT pH 1.2
(Averaged data for 6 samples)

| TIME (Min) | AMOUNT RELEASED (mg) | STD DEV | % RELEASED | STD DEV |
|---|---|---|---|---|
| 5 | 16.84 | (3.80) | 16.24 | (3.71) |
| 15 | 101.79 | (4.60) | 98.16 | (4.38) |
| 20 | 103.94 | (3.48) | 100.23 | (3.10) |
| 30 | 105.47 | (1.92) | 101.71 | (1.67) |
| 40 | 105.75 | (1.53) | 101.98 | (1.34) |
| 60 | 106.41 | (1.14) | 102.62 | (1.33) |

TABLE 11

DISSOLUTION DATA FOR Minomycin ®, i.e, MINOCYCLINE POWDER CAPSULES MEASURED AT pH 5.5
(Averaged data for 6 samples)

| TIME (Min) | AMOUNT RELEASED (mg) | STD DEV | % RELEASED | STD DEV |
|---|---|---|---|---|
| 5 | 7.67 | (4.60) | 7.43 | (4.45) |
| 10 | 55.14 | (8.67) | 53.46 | (8.38) |
| 15 | 80.70 | (8.32) | 78.25 | (8.07) |
| 30 | 96.06 | (4.44) | 93.14 | (4.29) |
| 40 | 99.07 | (1.83) | 96.06 | (1.77) |
| 50 | 100.22 | (1.39) | 97.18 | (1.33) |
| 60 | 100.59 | (1.23) | 97.54 | (1.16) |

STD DEV = Standard Deviation

EXAMPLE 3

Clinical Trials

For the initial trial in man, Pellet Compositions A and B were formulated to provide information on absorption site.

To this end, Pellet Composition A was formulated not to dissolve in the stomach and to dissolve exceedingly fast in the small intestine.

Pellet Composition B was formulated to control the dissolution of minocycline in the stomach. The controlled dissolution in the stomach meant that minocycline would appear in the region immediately after the pyloric sphincter wherein the pH is normally somewhere between 1.2 and 5.5. A pH of 1.2 has been selected to simulate the pH of the fasted stomach. The dissolution at or after pH 5.5 was substantially similar to that measured for Pellet Composition A.

Test Results in Man

The bioavailability of compositions A and B were compared to that of capsules of Minocycline hydrochloride formulated in a powder (Minocycline hydrochloride powder is extremely soluble under acidic conditions).

Composition B more closely approached the bioavailability of Minocycline hydrochloride capsules.

Regulatory authorities assess products by comparing bioequivalences—the same rate and extent of absorption as a reference product. Thus, for extent, the test product must not be less than 80% of the reference product.

SUMMARY

A single dose, balanced, three-way crossover study involving 18 healthy, adult volunteers (6 female, 12 male) compared the bioavailability of minocycline in three formulations administered in the fasting state.

The two test products were Pellet composition A capsules and B capsules, containing modified-release pellets of minocycline hydrochloride equivalent to 100 mg minocycline base and having preferred compositions as described above. The reference product was Lederle Minomycin ® capsules containing minocycline hydrochloride equivalent to 100 mg minocycline base.

The study was divided into three periods with a one week interval separating each period. Subjects were randomized by weight into three equal groups which were then randomly assigned to either dosage regimen A, B or C. Dosing regimen sequence followed a three by three Latin Square design where three regimen sequences were employed. The dosing regimens A, B and C were as follows:

Regimen A: (2×100 mg) A capsules were administered as a single oral dose with 180 mL of water following a 12-hour overnight fast.

Regimen B: (2×100 m) B capsules were administered as a single oral dose with 180 mL of water following a 12-hour overnight fast.

Regimen C: (2×100 mg) Minomycin ® capsules were administered as a single oral dose with 180 mL of water following a 12-hour overnight fast.

For regimens A, B and C, blood samples (6 mL) were collected from an indwelling venous catheter at 0, 0.5, 1.0, 1.5, 2.0, 2.5, 3.0, 3.5, 4.0, 6.0, 8.0, 10.0 and 12.0 hours following administration of the dose. Further blood samples were collected by venipuncture technique at 24.0, 28.0, 32.0, 34.0 and 48.0 hours after the dose.

In view of the unexplained, aberrant nature of the bioavailability data for subject 5, his data were excluded from the statistical analysis and only data from the remaining 17 subjects were discussed.

Examination of the AUC data (refer to Table 12) indicates only a small but important difference between the two test formulations (A and B capsules). Both of these products had significantly lower bioavailability relative to the reference product (Minomycin ® capsules). The mean relative bioavailability value for A capsules was $82.8 \pm 13.5\%$ while for B capsules the extent of absorption was $88.3 \pm 8.1\%$.

Although the reference product produced significantly higher mean $C_{max}$ values of minocycline than the test product (A capsules), there was no statistically significant difference between the mean $C_{max}$ values observed for B capsules and the reference product.

There was no significant difference in the mean $t_{max}$ values for the three products tested even though A capsules showed lag times of up to 2 hours in some subjects.

TABLE 12

| | MEAN (+SD) PHARMACOKINETIC PARAMETERS N = 17 | | | |
|---|---|---|---|---|
| | REGIMENS | | | STATISTICAL ANALYSIS Significance Level $p < 0.05$ |
| PARAMETERS | A Composition A fasting | B Composition D fasting | C Minomycin ® fasting | |
| F % Relative Bioavailability | 82.8 (13.5)[a] | 88.3 (8.1) | — | student's paired t-test NOT SIGNIFICANT A = B |
| $AUC_{0-\infty}$ (mg · h/L) | 50.32 (8.84) | 54.28 (9.74) | 61.60 (10.69) | ANOVA SIGNIFICANT A = B, A < C, B < C[b] |
| $C_{max}$ (mg/L) | 2.93 (0.78) | 3.08 (0.88) | 3.68 (0.95) | ANOVA SIGNIFICANT A = B, A < C, B = C |
| $t_{max}$ (h) | 3.13 (0.69) | 2.62 (1.05) | 2.44 (1.13) | ANOVA NOT SIGNIFICANT |
| $t_{\frac{1}{2}}$ (h) | 4.83 (2.09) | 14.92 (2.20) | 15.72 (2.39) | ANOVA NOT SIGNIFICANT |
| Ke ($h^{-1}$) | 0.0476 (0.007) | 0.0474 (0.007) | 0.0450 (0.007) | ANOVA NOT SIGNIFICANT |

LEGEND FOR TABLE 12
[a]Standard deviation
[b]Scheffe's F-test for significance
Composition A capsules show lag times from 0 to 2 hours.

TABLE 12-continued

Composition B capsules do not show a lag time.

$AUC_{0-\infty}(mg \cdot h/L)$ = Area under the curve to infinite time, caluclated using trapezoidal rule from 0 hours to the last measurable concentration and extrapolated to infinite time by the addition of the quantity: last measured concentration divided by the elimination rate constant.

$Ke(h^{-1})$ = Elimination rate constant: Apparent first order elimination rate constant calculated as the slope of a log-linear regression line fitted to at least the last four measured data points of the serum concentration versus time profiles.

$t_{\frac{1}{2}}(h)$ = Elimination half life: 0.693/elimination rate constant.

$C_{max}(mg/L)$ = Maximum observed serum concentration was obtained from visual inspection of the serum concentration versus time points.

$t_{max}(h)$ = Time to reach maximum observed serum concentration was obtained from visual inspection of the serum concentration versus time data points.

$F\%$ = Relative bioavailability value shown as a percent.

$$= \frac{AUC_{0-\infty}(test)}{AUC_{0-\infty}(ref.)} \times \frac{Dose\ (ref.)}{Dose\ (test)} \times 100$$

The mean elimination half lives calculated from log linear regression of the terminal concentration time data were not significantly different for each treatment. The half life values obtained are compatible with values reported for minocycline in the literature.

Thus, the test product, B capsules, is the preferred formulation since it does not show a lag time and demonstrates a slightly higher, but not statistically significant, mean relative bioavailability and mean maximum observed concentration value than A capsules.

The dissolution profile generated for pellet composition A may be viewed as slightly below the minimum dissolution required to provide substantial bioequivalence with the reference product (Minomycin ® capsules).

The dissolution profile generated for pellet composition B may be viewed as slightly above the minimum dissolution required to provide substantial bioequivalence with the reference product (Minomycin ® capsules).

The composition of the core coating may accordingly be modified slightly between that of A or B in order to define the minimum dissolution profile for the pharmaceutical pellet composition according to the present invention in the manner discussed above. The amount of the at least partially insoluble component and/or the insoluble component may be increased to improve bioequivalence with Minomycin ® for example. The composition of the core coating may be modified further to improve the bioequivalence with the reference product. Compositions C, D and E were formulated to improve bioequivalence with the reference product.

Finally, it is to be understood that various other modifications and/or alterations may be made without departing from the spirit of the present invention as outlined herein.

What is claimed is:

1. A pharmaceutical composition comprising
a core element including at least one tetracycline antibiotic; and
a core coating for the core element which is partially soluble at an acidic pH and ranges between about 5 and about 20% by weight of the core element, said core coating comprising approximately 15 to 85% by weight, based on the total weight of the core coating, excluding filler, of at least one acid insoluble polymer selected from cellulose acetate phthalate, hydroxypropyl methylcellulose phthalate, polyvinyl acetate phthalate, methacrylic acid copolymer type A, methacrylic acid: acrylic acid methyl ester copolymer, hydroxypropyl methylcellulose acetate succinate, cellulose acetate trimellitate or mixtures thereof; and
approximately 1 to 50% by weight, based on the total weight of the core coating, excluding filler, of an at least partially acid soluble component selected from polyvinylpyrrolidone, hydroxypropyl cellulose, hydroxypropyl methyl cellulose, methyl cellulose, sugars and mixtures thereof, wherein the composition has a dissolution profile of between 20% and 75% dissolved in 20 minutes at pH 1.2 and greater than 75% dissolved after 30 minutes at pH 5.5 so that the tetracycline antibiotic in the composition is released at a relatively low rate at a pH range of approximately 1 to 4 and at a relatively faster rate at a pH range of approximately 4.5 to 7.5.

2. A pharmaceutical composition according to claim 1 wherein the at least one tetracycline antibiotic is selected from tetracycline, chlortetracycline, demeclocycline, methacycline, oxytetracycline, minocycline or mixtures thereof.

3. A pharmaceutical composition according to claim 1 wherein said core coating ranges between about 7% and about 14% by weight of the core element.

4. A pharmaceutical composition according to claim 1 wherein the core element is a pellet, tabletted pellet or tablet.

5. A pharmaceutical composition according to claim 2 wherein the tetracycline antibiotic includes minocycline.

6. A pharmaceutical composition according to claim 1 wherein the core element also includes at least one core seed and at least one binding agent.

7. A pharmaceutical composition according to claim 1 wherein the core element also includes at least one binding agent and at least one filler.

8. A pharmaceutical composition according to claim 1 wherein the core element also includes a filler.

9. A pharmaceutical composition according to claim 6 wherein the tetracycline antibiotic is present in amounts of approximately 5 to 95% by weight based on the total weight of the core element; and
at least one core seed is present in amounts of from approximately 5 to 95% by weight based on the total weight of the core element.

10. A pharmaceutical composition according to claim 9 wherein the core element has the formulation:

| | |
|---|---|
| minocycline powder | 25-94% |
| sugar seeds | 5-74% |
| hydroxypropyl cellulose | 0.1-20% |

11. A pharmaceutical composition according to claim 9 wherein the core element has the formulation:

| | |
|---|---|
| minocycline powder | 25-94% |
| sugar seeds | 5-74% |
| povidone | 0.1-20% |

12. A pharmaceutical composition according to claim 7 wherein the core element has the formulation:

| | |
|---|---|
| minocycline powder | 25-94% |
| microcrystalline cellulose | 1-40% |
| hydroxypropyl cellulose | 1-10% |

13. A pharmaceutical composition according to claim 1 wherein the core coating further includes
up to approximately 50% by weight based on the total weight of the core coating, excluding filler, or at least one plasticizer selected from diethyl phthalate, triethyl citrate, triethyl acetyl citrate, triacetin, tributyl citrate, polyethylene glycol and glycerol; and
up to approximately 50% by weight based on the total weight of the core coating of at least one filler selected from silicon dioxide, talc, alumina, starch, kaolin, polacrilin potassium, powdered cellulose, microcrystalline cellulose and mixtures thereof.

14. A pharmaceutical composition according to claim 13 wherein the core coating has a formulation:
hydroxypropyl methyl
cellulose phthalate 50-80%
polyvinylpyrrolidone 10-40%
diethyl phthalate 1-30%

15. A pharmaceutical composition according to claim 1, wherein the core coating includes
approximately 15 to 85% by weight, excluding filler, of at least one acidic insoluble polymer selected from cellulose acetate phthalate, hydroxypropyl methyl cellulose phthalate, polyvinyl acetate phthalate, methacrylic acid copolymer type A, methacrylic acid: acrylic acid methyl ester copolymer, hydroxypropyl methylcellulose acetate succinate, cellulose acetate trimellitate or mixtures thereof; and
approximately 1 to 50% by weight, based on the total weight of the core coating, excluding filler, of polyvinylpyrrolidone.

16. A method of treating bacterial infections in patients requiring such treatment which method includes administering to a patient an effective amount of a pharmaceutical composition comprising
a core element including a tetracycline antibiotic; and
a core coating for the core element which is partially soluble at a highly acidic pH and ranges between about 5 and about 20% by weight of the core element, said core coating comprising approximately 15 to 85% by weight, based on the total weight of the core coating, excluding filler, of at least one acid insoluble polymer selected from cellulose acetate phthalate, hydroxypropyl methylcellulose phthalate, polyvinyl acetate phthalate, methacrylic acid copolymer type A, methacrylic acid: acrylic acid methyl ester copolymer, hydroxypropyl methylcellulose acetate succinate, cellulose acetate trimellitate or mixtures thereof; and
approximately 1 to 50% by weight, based on the total weight of the core coating, excluding filler, of an at least partially acid soluble component selected from polyvinylpyrrolidone, hydroxypropyl cellulose, hydroxypropyl methyl cellulose, methyl cellulose, sugars and mixtures thereof, wherein the composition has a dissolution profile of between 20% and 75% dissolved in 20 minutes at pH 1.2 and greater than 75% dissolved after 30 minutes at pH 5.5 so that the tetracycline antibiotic in the composition is released at a relatively low rate at a pH range of approximately 1 to 4 and at a relatively faster rate at a pH range of approximately 4.5 to 7.5.

17. A method according to claim 1 wherein at least one tetracycline antibiotic is selected from tetracycline, chlortetracycline, demeclocycline, methacycline, oxytetracycline, minocycline and mixtures thereof.

18. A pharmaceutical composition according to claim 1, wherein said core coating is between about 7% and about 14% by weight of the core.

* * * * *